US006989445B2

(12) United States Patent
Dantanarayana et al.

(10) Patent No.: US 6,989,445 B2
(45) Date of Patent: Jan. 24, 2006

(54) SUBSTITUTED [1,4]OXAZINO[2,3-G]INDAZOLES FOR THE TREATMENT OF GLAUCOMA

(75) Inventors: Anura P. Dantanarayana, Kandy (LK); Jesse Albert May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 40 days.

(21) Appl. No.: 11/011,804

(22) Filed: Dec. 14, 2004

(65) Prior Publication Data

US 2005/0130960 A1 Jun. 16, 2005

Related U.S. Application Data

(60) Provisional application No. 60/529,507, filed on Dec. 15, 2003.

(51) Int. Cl.
*C07D 498/04* (2006.01)
*A61K 31/5383* (2006.01)
*A61P 27/06* (2006.01)

(52) U.S. Cl. ..................................... 544/101; 544/60
(58) Field of Classification Search ............... 544/101, 544/60
See application file for complete search history.

(56) References Cited

U.S. PATENT DOCUMENTS

| | | | |
|---|---|---|---|
| 4,690,931 A | 9/1987 | Wick et al. .................. 514/317 |
| 5,011,846 A | 4/1991 | Gittos et al. ................... 471/18 |
| 5,151,444 A | 9/1992 | Ueno et al. ................... 514/530 |
| 5,290,781 A | 3/1994 | Espino et al. ................ 514/259 |
| 5,296,504 A | 3/1994 | Stjernschantz et al. ..... 514/530 |
| 5,352,708 A | 10/1994 | Woodward et al. ......... 514/729 |
| 5,422,368 A | 6/1995 | Stjernschantz et al. ..... 514/530 |
| 5,494,928 A | 2/1996 | Bös ............................. 514/415 |
| 5,538,974 A | 7/1996 | Ogawa et al. ............... 514/253 |
| 5,561,150 A | 10/1996 | Wichmann ................... 514/406 |
| 5,571,833 A | 11/1996 | Kruse et al. ................. 514/414 |
| 5,578,612 A | 11/1996 | Macor et al. ................ 514/323 |
| 5,646,173 A | 7/1997 | Bös et al. .................... 514/411 |
| 5,652,272 A | 7/1997 | Ogawa et al. ............... 514/652 |
| 5,693,654 A | 12/1997 | Birch .......................... 514/323 |
| 5,874,477 A | 2/1999 | McConnell et al. ......... 514/657 |
| 5,889,052 A | 3/1999 | Klimko et al. .............. 514/530 |
| 5,902,815 A | 5/1999 | Olney et al. ................. 514/285 |
| 6,107,324 A | 8/2000 | Behan et al. ................ 514/406 |
| 6,245,796 B1 | 6/2001 | Maeno et al. ............... 514/403 |
| 6,518,294 B2 | 2/2003 | Teng et al. .................. 514/403 |
| 6,660,870 B1 | 12/2003 | Ruskinko et al. ......... 548/307.4 |
| 6,664,286 B1 | 12/2003 | May et al. ................... 514/415 |
| 6,696,476 B2 | 2/2004 | Chen et al. ................. 514/403 |
| 6,806,285 B1 | 10/2004 | May et al. ................... 514/416 |
| 2003/0083346 A1 | 5/2003 | May et al. ................... 514/320 |
| 2003/0181503 A1 | 9/2003 | May et al. ................... 514/406 |

FOREIGN PATENT DOCUMENTS

| | | |
|---|---|---|
| EP | 0 771 563 B1 | 1/2003 |
| WO | WO 92/00338 | 1/1992 |
| WO | WO 94/03162 | 2/1994 |
| WO | WO 94/13275 | 6/1994 |
| WO | WO 97/35579 | 10/1997 |
| WO | WO 09/18458 | 5/1998 |
| WO | WO 98/31354 | 7/1998 |
| WO | WO 99/59499 | 11/1999 |
| WO | WO 00/12475 | 3/2000 |
| WO | WO 00/12510 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/40183 | 6/2001 |
| WO | WO 01/70207 | 9/2001 |
| WO | WO 01/070222 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 01/85152 | 11/2001 |
| WO | WO 03/051291 | 6/2002 |
| WO | WO 03/051352 | 6/2002 |
| WO | WO 03/053436 | 7/2002 |
| WO | WO 02/098350 | 12/2002 |
| WO | WO 02/098400 | 12/2002 |
| WO | WO 02/098860 | 12/2002 |
| WO | WO 01/83487 | 7/2003 |
| WO | WO 04/019874 | 3/2004 |
| WO | WO 04/028451 | 4/2004 |
| WO | WO 04/054572 | 7/2004 |
| WO | WO 04/058725 | 7/2004 |

OTHER PUBLICATIONS

Bowen et al. "Nonlinear regression using spreadsheets," *Trends in Pharmacological Sciences*, vol. 16, pp. 413-417 (1995).

Chang et al., "Mechanism of the Ocular Hypotensive Action of Ketanserin", *J. of Ocular Pharmacology*, vol. 1(2), pp. 137-147 (1985).

Fiorella et al., "Role of 5-$HT_{2A}$ and 5-$HT_{2C}$ receptors in the stimulus effects of hallucinogenic drugs II: reassessment of LSD false positives," *Psychopharmacology*, vol. 121, pp. 357-363 (1995).

(Continued)

*Primary Examiner*—Mark L. Berch
*Assistant Examiner*—Kahsay Habte
(74) *Attorney, Agent, or Firm*—Patrick M. Ryan

(57) ABSTRACT

Substituted [1,4]oxazino[2,3-g]indazols for lowering intraocular pressure and treating glaucoma are disclosed.

2 Claims, No Drawings

OTHER PUBLICATIONS

Gupta et al., "Therapeutic Potentials of 5-HT Receptor Modulators," *Indian J. of Pharmacology*, vol. 26, pp. 94-107 (1994).

Johnson et al., "Binding to the Serotonin 5-$HT_2$ Receptor by the Enantiomers of $125_{1-DOI}$," *Neuropharmacology*, vol. 26(12), pp. 1803-1806 (1987).

Krootila et al., "Effect of Serotonin and Its Antagonist (Ketanserin) on Intraocular Pressure in the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-$HT_2$ Antagonist on Intraocular Pressure in Rabbits," *IOVS*, vol. 36(40, S719 (1995).

May et al., "A Novel and Selective 5-$HT_2$ Receptor Agonist with Ocular Hypotensive Activity: (S)-(+)-1-(2-Aminopropyl)-8,9-dihydropyranol[3,2-e]indole," *J. Med. Chem.*, vol. 46, pp. 4188-4195 (2003).

May et al., "Evaluation of the Ocular Hypotensive Response of Serotonin 5-$HT_{1A}$ and 5-$HT_2$ Receptor Ligands in Conscous Ocular Hypertensive Cynomolgus Monkeys, *J. of Pharmacolgy and Experimental Therapeutics*," vol. 306(1), pp. 301-309 (2003).

Osborne et al., "Do Beta-Adrenoceptors and Serotonin 5-$HT_{1A}$ Receptors Have Similar Fumctions in the Control of Intraocular Pressure in the Rabbit," *Ophthalmolgica*, vol. 210, pp. 308-314 (1996).

Osborne et al., "5-Hydroxytryptamine$_{1A}$ agoists: potential use in glaucoma. Evicence from animal studies," *Eye*, vol. 14(38), pp. 454-463 (2000).

Takeda et al., "The Effect of Inplag. Novel Selective 5-$HT_2$ Antagonist on Intraocular Pressure in Glaucoma Patients," *IOVS*, Vo. 36(4), S734 (1995).

Wang et al., "Effect of 5-methylurapidil, an $\alpha_{1a}$adrenergic antagonist and 5-hydroxytryptamine$_{1a}$ agonist, on aqueous humor dynamics in monkeys and rabbits," *Current Eye Research*, vol. 16, pp. 769-775 (1997).

Wang et al., "Effect of $_p$-MPPI Hydrochloride (p-MPPI) applied before 5-Methylurapidil (5-MU) on Intraocular Pressure (IOP) in Normal Monkeys," *IOVS*, vol. 39(40, S488 (1998).

SUBSTITUTED [1,4]OXAZINO[2,3-G]INDAZOLES FOR THE TREATMENT OF GLAUCOMA

This application claims the benefit of U.S. Provisional Application No. 60/529,507, filed Dec. 15, 2003.

BACKGROUND OF THE INVENTION

The present invention relates to the use of substituted [1,4]oxazino[2,3-g]indazols for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but attribute the IOP effect to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see U.S. Pat. No. 6,664,286, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives, and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121: 357, 1995].

U.S. Pat. Nos. 5,561,150 and 5,646,173 relate to certain tricyclic pyrazole derivative compounds which are identified as being 5-$HT_{2C}$ agonists for the treatment of CNS diseases and are primarily directed to lipophilic analogs that have a high probability of entering the brain. Similarly, U.S. Pat. No. 6,245,796 and WO 01/83487 relate to tricyclic 5-$HT_{2C}$ agonists for the treatment of CNS diseases. All the patents and publications mentioned above and throughout are incorporated in their entirety by reference herein.

Few oxazine containing fused indazoles have been reported. U.S. Pat. No. 6,518,294 relates to a broadly identified series of aryl and arylalkyl substituted fused tricyclic pyrazoles that includes certain aryl and arylalkyl substituted [1,4]oxazino[2,3-g]indazols. None of these are specifically identified in the '294 patent, however. The compounds described in the '294 patent are reported to increase intracellular levels of cGMP.

SUMMARY OF THE PRESENT INVENTION

A feature of the present invention is to provide novel compounds which are 5-$HT_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

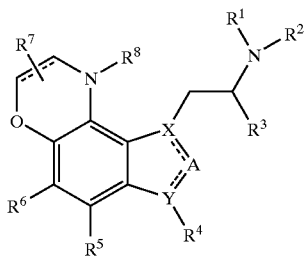

The present invention further relates to pharmaceutical compositions containing at least one compound of Formula I.

The present invention further relates to methods to lower and/or control normal or elevated intraocular pressure by administering an effective amount of a composition containing a compound having Formula I as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are represented by the following Formula I:

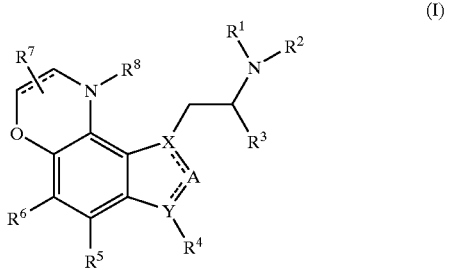

wherein $R^1$ and $R^2$ are independently hydrogen or $C_{1-4}$alkyl;

$R^3$ is hydrogen or $C_{1-4}$alkyl, or $R^2$ and $R^3$ together can complete a pyrrolidine or piperidine ring, which can be substituted with $C_{1-4}$alkyl;

$R^4$ is hydrogen, halogen, or $C_{1-4}$alkyl;

$R^5$ and $R^6$ are independently hydrogen, halogen, $C_{1-6}$alkyl, $C_{1-6}$alkylthio, $C_{1-6}$alkylsulfonyl, $C_{1-6}$alkylsulfoxide, nitrile, or $C_{1-6}$alkyl substituted with halogen;

$R^7$ is hydrogen, C=$OR^9$, =O (carbonyl), $C_{1-6}$alkyl, or substituted $C_{1-6}$alkyl wherein the substituent is at least one of hydroxyl, $C_{1-6}$alkoxy, $NR^{12}R^{13}$, $CO_2H$, $CO_2C_{1-6}$alkyl, $C(=O)NR^{12}R^{13}$, $S(O)_mNR^{12}R^{13}$, and a saturated or unsaturated 5 or 6-membered heteroaryl ring which can contain 1–4 heteroatoms selected from N, O, or S and can be unsubstituted or substituted with $C_{1-4}$alkyl or phenyl; $R^8$ is hydrogen, $C_{1-6}$alkyl, or substituted $C_{1-6}$alkyl wherein the substituent is at least one of hydroxyl, $C_{1-6}$alkoxy, $NR^{12}R^{13}$, $CO_2H$, $CO_2C_{1-6}$ alkyl, and $C(=O)NR^{12}R^{13}$;

$R^9$ is hydroxyl, $C_{1-6}$alkoxy, $NR^{14}R^{15}$, $C_{1-6}$alkyl, or substituted $C_{2-6}$alkyl wherein the substituent is at least one of hydroxyl, $C_{1-6}$alkoxy, $NR^{12}R^{13}$, $CO_2H$, $CO_2C_{1-6}$ alkyl, $S(O)_mNR^{12}R^{13}$, halogen, and a heterocyclic ring selected from pyrrolidin-2-yl, imidazo-2-yl, imidazo-4-yl, morpholin-3-yl, oxazolyl, isoxazolyl, thiazolyl, or tetrazolyl, which can be unsubstituted or substituted with $C_{1-4}$alkyl;

$R^{12}$ and $R^{13}$ are independently hydrogen, $C_{1-6}$alkyl, or substituted $C_{2-6}$alkyl wherein the substituent is at least one of hydroxyl, $C_{1-6}$alkoxy, and halogen, or $R^{12}$, $R^3$, and the intervening nitrogen atom together can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

$R^{14}$ and $R^{15}$ are independently hydrogen, $C_{1-6}$alkyl, hydroxyl, $C_{1-6}$alkoxy, or substituted $C_{2-6}$alkyl wherein the substituent is at least one of hydroxyl, $C_{1-6}$alkoxy, halogen and a heterocyclic ring selected from pyrrolidin-2-yl, imidazo-2-yl, imidazo-4-yl, morpholin-3-yl, oxazolyl, isoxazolyl, thiazolyl, tetrazolyl, which can be unsubstituted or substituted with $C_{1-4}$alkyl, or $R^{14}$, $R^{15}$, and the intervening nitrogen atom together can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

A is N or CH;

X and Y are either N or C, provided that X and Y cannot be the same;

and the dashed bonds denote a suitably appointed single and double bond.

Pharmaceutically acceptable salts and solvates, and prodrug forms of the compounds of Formula I are also part of the present invention. Certain compounds of Formula I can contain one or more chiral centers. The present invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

Preferred compounds of Formula I are:
1) (S)-2-(8,9-dihydro-9-methyl-7H-[1,4]oxazino[2,3-g]indazol-1-yl)-1-methylethylamine fumarate;
2) 1-((S)-2-Aminopropyl)-1,9-dihydro-7H-[1,4]oxazino[2,3-g]indazol-8-one hydrochloride;
3) 1-((S)-2-Aminopropyl)-1,9-dihydro-9-methyl-7H-[1,4]oxazino[2,3-g]indazol-8-one hydrochloride; and
4) [1-[(2S)-2-aminopropyl]-9-methyl-1,7,8,9-tetrahydro[1,4]oxazino[2,3-g]indazol-8-yl]methanol.

The most preferred compound of Formula (I) is (S)-2-(8,9-dihydro-9-methyl-7H-[1,4]oxazino[2,3-g]indazol-1-yl)-1-methylethylamine fumarate.

Synthesis

Compounds of Formula I can be prepared by using one of several synthetic procedures. P denotes a suitable protective group to assure that a particular atom is not modified during the indicated chemical reaction.

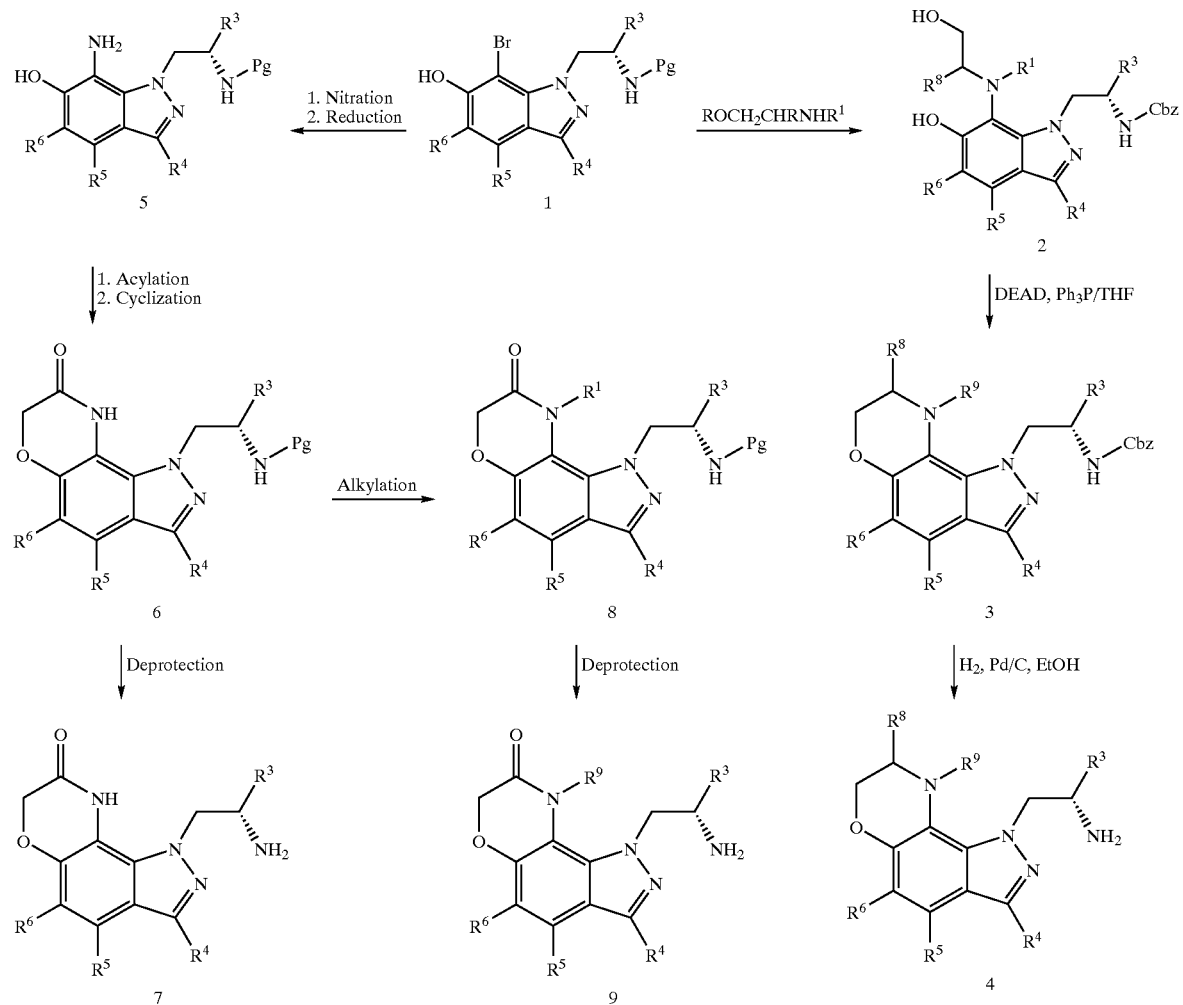

Scheme 1

Using the procedures described in Scheme 1 (above), the Examples 1–3 (below), and well known procedures, one skilled in the art can prepare the compounds disclosed herein.

The following examples are given to illustrate the preparation of compounds that are the subject of this invention but should not be construed as implying any limitations to the claims. The proton magnetic resonance spectrum of each compound of the Examples was consistent with the assigned structure.

EXAMPLE 1

(S)-2-(8,9-dihydro-9-methyl-7H-[1,4]oxazino[2,3-g] indazol-1-yl)-1-methylethylamine fumarate Step A: Benzyl 2-(7-bromo-6-hydroxy-1H-indazol-1-yl)-1-methylethylcarbamate To a stirred solution of benzyl 2-(6-hydroxy-1H-indazol-1-yl)-1-methylethylcarbamate (0.90 g, 2.98 mmol) in dichloromethane (10 mL) and tetrahydrofuran (5 mL) was added N-bromosuccinimide (0.59 g, 3.38 mmol) at room temperature. After 16 h, a saturated aqueous solution of ammonium chloride (25 mL) was added and this mixture was extracted with ethyl acetate (3×60 mL). The combined extracts were washed with brine (10 mL), dried (magnesium sulfate), and evaporated. The residue was purified by chromatography (silica, 30% to 50% ethyl acetate in hexane) to give (1.1 g, 91%): $^1$H NMR (CDCl$_3$) δ 7.86 (1H, d, J=8.8 z), 7.80 (1H, s), 7.37 (6H, m), 6.18 (1H, brs), 5.24 (1H, brs), 4.95 (2H, s), 4.80 (2H, m), 4.34 (1H, m), 1.26 (3H, d, J=6.8 Hz); MS (ES) m/z 404, 406 (M$^+$).

Step B: Benzyl (S)-2-[6-hydroxy-7-[(2-hydroxyethyl)methylamino]-1H-indazol-1-yl]-1-methylethylcarbamate To a stirred solution of the product from Step A (0.24 g, 0.59 mmol) was added 2-(methyamino)ethanol (2.0 mL) and the solution was heated at 80° C. for 18 h. A saturated aqueous solution of ammonium chloride (20 mL) was added to the reaction mixture, which was extracted with ethyl acetate (3×50 mL). The combined extracts were washed with brine (10 mL), dried (MgSO$_4$) and evaporated to give a residue which was purified by chromatography (silica, 30% ethyl acetate in hexane) to give an oil (0.16 g, 68%): $^1$H NMR (CDCl$_3$) δ 8.50 (1H, brs), 8.01(1H, s), 7.30 (6H, m), 6.77 (1H, d, J=8.4 Hz), 5.02 (2H, m), 4.59 (2H, m), 4.77 (1H, brs), 4.09 (1H, m), 3.69 (1H, m), 3.36 (2H, m), 2.93 (3H, s), 1.26 (3H, d, J=6.4 Hz); MS (ES) m/z 399 (M$^+$).

Step C: Benzyl (S)-2-(8,9-dihydro-9-methyl-7H-[1,4]oxazino[2,3-g]indazol-1-yl)-1-methylethylcarbamate To a stirred solution of the product from Step B (0.36 g, 0.82 mmol) in tetrahydrofuran (10 mL) at 0° C. was added triphenylphospine (0.26 g, 0.98 mmol) followed by diethyl azodicarboxylate (0.23 mL, 1.23 mmol). After 2 h, a saturated aqueous solution of ammonium chloride (30 mL) was added and the mixture was extracted with ethyl acetate (3×65 mL). The combined extracts were washed with brine (10 mL), dried (MgSO$_4$), and evaporated to a residue which was purified by chromatography (silica, 30%–50% ethyl acetate in hexane) to give an oil (0.28 g, 89%): $^1$H NMR (CDCl$_3$) δ 7.88 (1H, s), 7.30 (6H, m), 6.73 (1H,d, J=8.4 Hz), 4.91 (2H, s), 4.63 (2H, m), 4.37 (2H, m), 4.09 (1H,m), 3.26 (2H,m), 2.73 (3H,s), 1.06 (3H, d, J=6.4 Hz); MS (ES) m/z 381 (M$^+$).

Step D: (S)-1-Methyl-2-(8,9-dihydro-9-methyl-7H-[1,4]oxazino[2,3-g]indazol 1-yl)ethylamine fumarate To a solution of the product from Step C (0.11 g, 0.28 mmol) in ethanol was added palladium-on-carbon (10%, 0.01 g) under a nitrogen atmosphere at room temperature. The resulted suspension was stirred for 20 h under an atmosphere of hydrogen. The reaction mixture was filtered through diatomaceous earth and the filtrate was concentrated in vacuo to give an oil (0.06 g, 92%), which was treated with fumaric acid and the resultant salt was crystallized from a mixture of methanol and ethyl acetate to give a white solid: m.p:185–187° C.; $^1$H NMR (DMSO-d$_6$) δ8.00 (1H, s), 7.31(1H, d, J=8.8 Hz), 6.65 (1H, d, J=8.8 Hz), 6.47 (1H, s), 4.65 (2H, m), 4.25 (2H, t, J=4.4 Hz), 3.55 (1H, m), 3.14 (2H, d, J=1.6 Hz), 2.75 (3H, s), 0.90 (3H, d, J=6.4 Hz); MS (ES) m/z 247 (M$^+$). Analysis. Calculated for C$_{13}$H$_{18}$N$_4$O.C$_4$H$_4$O$_4$.0.1H$_2$O: C, 56.07; H, 6.14; N, 15.38. Found: C, 55.89; H, 6.12; N, 15.28.

EXAMPLE 2

1-((S)-2-Aminopropyl)-1,9-dihydro-7H-[1,4]oxazino [2,3-g]indazol-8-one hydrochloride Step A: tert-Butyl (S)-[2-(6-hydroxyindazol-1-yl)-1-methylethylcarbamate To a stirred suspension of 1-((S)-2-(aminopropyl)-1H-indazol-6-ol (5.0 g, 26.2 mmol) and di-tert-butyldicarbonate (6.28 g, 28.8 mmol) in anhydrous tetrahydrofuran (100 mL) at ambient temperature was added triethylamine (2.91 g, 4.01 mL, 28.8 mmol). After 30 min water (5 mL) was added and the mixture was stirred for an additional 30 min, evaporated to dryness, mixed with a saturated aqueous solution of sodium bicarbonate (80 mL), and extracted with ethyl acetate (3×100 mL). The combined extracts were dried over magnesium sulfate, filtered and evaporated to dryness to give a yellowish solid. The solid was triturated with a mixture of ethyl acetate and hexane (1:3), filtered, and dried to give a solid (5.96 g). The filtrate was purified by chromatography (silica, gradient 20% to 50% ethyl acetate in hexane) to give a solid (1.30 g): mp 153° C.; LC/MS (+APCI) 292 (M+H).

Step B: tert-Butyl [2-(7-bromo-6-hydroxyindazol-1-yl)-1-methylethylcarbamate

To a solution of the product from Step A (6.0 g, 20.6 mmol) in anhydrous tetrahydrofuran (100 mL) at 0° C. was added N-bromosuccinimide (3.67 g, 20.6 mmol). After stirring for 30 min the ice bath was removed and the reaction mixture was stirred at ambient temperature for 1 h. The reaction mixture was evaporated and the residue was mixed with a saturated aqueous solution of sodium bicarbonate (100 mL) and extracted with ethyl acetate (3×100 mL). The combined extracts were dried over magnesium sulfate, filtered and evaporated to give an oil (8.12 g), which was used in the next step.

Step C: tert-Butyl [2-(6-hydroxy-7-nitroindazol-1-yl)-1-methyl-ethylcarbamate

To a stirred solution of the product from Step B (1.63 g, 4.41 mmol) in a mixture of tetrahydrofuran (20 mL) and acetic acid (20 mL) was added sodium nitrite (0.304 g, 4.41 mmol) at ambient temperature. After 1 h another portion of sodium nitrite (0.304 g, 4.41 mmol) was added and the reaction was continued for additional 30 minutes. The reaction mixture was poured into ice-water and extracted with ethyl acetate (3×80 mL). The combined extracts were washed with a saturated aqueous solution of sodium bicarbonate till no bubbles formed and dried over magnesium sulfate. Evaporation gave an oil (1.74 g) that was used in the next reaction without further purification.

Step D: tert-Butyl 1-methyl-[2-(amino-6-hydroxyindazol-1-yl)]-1-methylethylcarbamate A solution of the product from Step C (1.74 g, 4.41 mmol) in methanol (60 mL) was combined with palladium-on-carbon (10%, 0.17 g) and this mixture was placed under hydrogen gas at atmospheric pressure overnight. The reaction mixture was filtered and concentrated to give an oil (1.60 g): LC/MS (+APCI) m/z 307 (M+H).

Step E: tert-Butyl [2-[7-(2-Chloroacetylamino)-6-hydroxyindazol-1-yl]-1-methyl ethylcarbamate The product from Step D (1.60 g) was dissolved in acetone (50 mL) and mixed with an aqueous solution of sodium bicarbonate (10 mL). The mixture was cooled (ice bath) and chloroacetyl chloride (0.351 mL, 4.41 mmol) was added with stirring. After 30 min the ice bath was removed and the reaction mixture was stirred for 1 h and extracted with ethyl acetate (3×50 ml). The combined extracts were dried and concentrated to give a residue which was purified by chromatography (silica, 20% to 50% ethyl acetate in hexane) to give an oil (0.42 g, 25%, 2 steps): LC/MS (+APCI) m/z 383 (M+H).

Step F: tert-Butyl 2-(8,9-dihydro-8-oxo-7H-[1,4]oxazino[2,3-g]indazol-1-yl)-1-methylethylcarbamate The product from Step E (0.42 g, 1.10 mmol) was dissolved in acetone (50 mL) and is potassium carbonate (0.30 g, 2.17 mmol) was added; the suspension was heated at 50° C. for 2 h, concentrated, and mixed with a saturated aqueous solution of sodium bicarbonate (50 mL). This mixture was extracted with ethyl acetate (3×50 mL) and the combined extracts were dried and evaporated to give an oil, which was purified by chromatography (silica, 20% to 50% ethyl acetate in hexane) to give an oil which solidified (0.22 g): mp 147–148° C.; LC/MS (+APCI) m/z 347 (M+H).

Step G: 1-((S)-2-Aminopropyl)-1,9-dihydro-7H-[1,4]oxazino[2,3-g]indazol-8-one hydrochloride The product from Step F (0.14 g, 0.40 mmol) was dissolved in trifluoroacetic acid (5 mL), stirred overnight, and evaporated to dryness. The residue was mixed with a solution of hydrochloric acid in ethanol (5 mL) and evaporated to give an solid. Crystallization from ethanol gave an off-white solid (0.081 g): mp 293–295° C.; LC/MS (+APCI) m/z 247 (M+H). Analysis. Calculated for $C_{12}H_{14}N_4O_2$ HCl: H, 5.35; C, 50.98; N, 19.82. Found: H, 5.41; C, 50.88; N, 19.63.

EXAMPLE 3

1-((S)-2-Aminopropyl)-1,9-dihydro-9-methyl-7H-[1,4]oxazino[2,3-g]indazol-8-one hydrochloride Step A: tert-Butyl (S)-2-(8,9-dihydro-9-methyl-8-oxo-7H-[1,4]oxazino[2,3-g]indazol-1-yl)-1-methylethylcarbamate To a solution of the product from Example 2, Step F (0.22 g, 0.64 mmol) in anhydrous tetrahydrofuran (30 mL) was added sodium hydride (60% dispersion, 28 mg, 0.70 mmol) and this mixture was stirred under a nitrogen atmosphere for 10 min. Iodomethane (99 mg, 44 uL, 0.70 mmol) was added and the mixture was stirred for 1 h followed by the addition of anhydrous dimethylformamide (20 mL); this mixture was stirred for 4 h, poured into ice water, and the solution was extracted with ethyl acetate (3×50 mL). The combined extracts were evaporated to a residue that was purified by chromatography (gradient, 20% to 50% ethyl acetate in hexane to give an oil (0.14 g, 57%): LC/MS (+APCI) m/z 361 (M+H).

Step B: 1-((S)-2-Aminopropyl)-9-methyl-1,9-dihydro-7H-[1,4]oxazino[2,3-g]indazol-8-one hydrochloride The product from Step A (0.14 g, 0.39 mmol) was mixed with trifluoacetic acid (5 mL) and the resulting solution was stirred at ambient temperature overnight. The reaction mixture was evaporated to a residue that was purified by chromatography (gradient, water to 50% of acetonitrile/water (0.1% trifluoroacetic acid). The combined fractions were evaporated, mixed with a solution of hydrochloric acid in ethanol (3 mL), evaporated, and dried in vacuo at 78° C. to give a solid (63 mg, 53%): LC/MS (+APCI) m/z 261 (M+H). Analysis. Calculated for $C_{13}H_{16}N_4O_2 \cdot HCl \cdot 0.55H_2O$: C, 50.90; H, 5.95; N, 18.26. Found: C, 51.13; H, 6.05; N, 17.88.

The compounds of the present invention can be used to lower and control IOP including IOP associated with normotension glaucoma, ocular hypertension, and glaucoma in warm blooded animals including humans and other mammals. Since the treatment of glaucoma is preferably with compounds that do not enter the CNS, relatively polar compounds that are 5-$HT_2$ agonists are of particular interest. The compounds are preferably formulated in pharmaceutical compositions which are preferably suitable for topical delivery to the eye of the patient.

The compounds of this invention, Formula I, can be incorporated into various types of pharmaceutical compositions, such as ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g., nipradolol), $\alpha_2$ agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444, "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350, and appropriate compounds from WO 94/13275, including memantine.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma. Pharmaceutically acceptable amounts of the compounds of the present invention will be readily understood by those skilled in the art to mean amounts sufficient to effect the desired therapy without toxicity or other deleterious effects on the patients' health. Examples of such amounts include without limitation those amounts shown in the Examples.

Method 1

5-HT$_2$ Receptor Binding Assay

To determine the affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 μL) dispersed in 50 mM Tris HCl buffer (pH 7.4) are incubated with [$^{125}$I]DOI (80 μM final) in the absence or presence of methiothepin (10 μM final) to define total and non-specific binding, respectively, in a total volume of 0.5 mL. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or K$_i$ value.

Method 2

5-HT$_2$ functional Assay: [Ca$^{2+}$]$_i$ Mobilization

The receptor-mediated mobilization on intracellular calcium ([Ca$^{2+}$]$_i$) was studied using the Fluorescence Imaging Plate Reader (FLIPR) instrument. Rat vascular smooth muscle cells, A7r5, were grown in a normal media of DMEM/10% FBS and 10 μg/mL gentamycin. Confluent cell monolayers were trypsinized, pelleted, and re-suspended in normal media. Cells were seeded in a 50 μL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 μL) to each well of the 96-well plate and incubated with dye for 1 h at 23° C.

Typically, test compounds were stored at 25 μM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 μM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000–12000 counts by modifying the exposure time, the camera F-stop, or the laser power. Instrument settings for a typical assay were the following: laser power 0.3–0.6 W, camera F-stop F/2, and exposure time 0.4 sec. An aliquot (25 μL) of the test compound was added to the existing 100 μL dye-loaded cells at a dispensing speed of 50 μL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 μM 5-HT, they were incubated with the cells for 15 minutes prior to the addition of 5-HT.

Using the foregoing methods, 5-HT$_2$ binding affinities and agonist potential can readily be determined.

The above procedures were used to generate the data shown in Table 1.

TABLE 1

5-HT$_{2A}$ Receptor Binding and Functional Data

| Example | 5-HT$_{2A}$ | | |
|---|---|---|---|
| | IC$_{50}$ (nM) | EC$_{50}$ (nM) | E$_{max}$ (%) |
| 1 | 1 | 20 | 82 |
| 2 | 3.5 | 195 | 60 |
| 3 | 7.6 | 550 | 41 |

The following topical ophthalmic formulations are useful according to the present invention administered 1–4 times per day according to the discretion of a skilled clinician.

EXAMPLE 4

| Ingredients | Amount (wt %) |
| --- | --- |
| Compound of Example 1 | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 5

| Ingredients | Amount (wt %) |
| --- | --- |
| Compound of Example 1 | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 6

| Ingredients | Amount (wt %) |
| --- | --- |
| Compound of Example 1 | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 7

| Ingredients | Amount (wt %) |
| --- | --- |
| Compound of Example 1 | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound of the formula

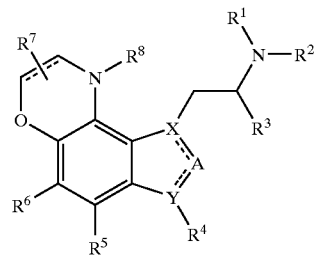

wherein
$R^1$ and $R^2$ are independently hydrogen or $C_{1-4}$alkyl;
$R^3$ is hydrogen or $C_{1-4}$alkyl, or $R^2$ and $R^3$ together can complete a pyrrolidine or piperidine ring, which can be substituted with $C_{1-4}$alkyl;
$R^4$ is hydrogen, halogen, or $C_{1-4}$alkyl;
$R^5$ and $R^6$ are independently hydrogen, halogen, $C_{1-6}$alkyl, $C_{1-6}$alkylthio, $C_{1-6}$alkylsulfonyl, $C_{1-6}$alkylsulfoxide, nitrile, or $C_{1-6}$alkyl substituted with halogen;
$R^7$ is hydrogen, C=$OR^9$, =O, $C_{1-6}$alkyl, or substituted $C_{1-6}$alkyl wherein the substituent is at least one of hydroxyl, $C_{1-6}$alkoxy, $NR^{12}R^{13}$, $CO_2H$, $CO_2C_{1-6}$alkyl, $C(=O)NR^{12}R^{13}$, $S(O)_mNR^{12}R^{13}$, and a saturated or unsaturated 5 or 6-membered heteroaryl ring which can contain 1–4 heteroatoms selected from N, O, or S and can be unsubstituted or substituted with $C_{1-4}$alkyl or phenyl;
$R^8$ is hydrogen, $C_{1-6}$alkyl, or substituted $C_{1-6}$alkyl wherein the substituent is at least one of hydroxyl, $C_{1-6}$alkoxy, $NR^{12}R^{13}$, $CO_2H$, $CO_2C_{1-6}$alkyl and $C(=O)NR^{12}R^{13}$;
$R^9$ is hydroxyl, $C_{1-6}$alkoxy, $NR^{14}R^{15}$, $C_{1-6}$alkyl, or substituted $C_{2-6}$ alkyl wherein the substituent is at least one of hydroxyl, $C_{1-6}$alkoxy, $NR^{12}R^{13}$, $CO_2H$, $CO_2C_{1-6}$alkyl, $S(O)_mNR^{12}R^{13}$, halogen, and a heterocyclic ring selected from pyrrolidin-2-yl, imidazo-2-yl, imidazo-4-yl, morpholin-3-yl, oxazolyl, isoxazolyl, thiazolyl, or tetrazolyl, which can be unsubstituted or substituted with $C_{1-4}$alkyl;
$R_{12}$ and $R_{13}$ are independently hydrogen, $C_{1-6}$alkyl, or substituted $C_{2-6}$alkyl wherein the substituent is at least one of hydroxyl, $C_{1-6}$alkoxy, and halogen, or $R^{12}$, $R^{13}$, and the intervening nitrogen atom together can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl, or $C_{1-4}$alkyl substituted with hydroxy or $C_{1-4}$alkoxy;
$R^{14}$ and $R^{15}$ are independently hydrogen, $C_{1-6}$alkyl, hydroxyl, $C_{1-6}$alkoxy, or substituted $C_{2-6}$alkyl wherein the substituent is at least one of hydroxyl, $C_{1-6}$alkoxy, halogen and a heterocyclic ring selected from pyrrolidin-2-yl, imidazo-2-yl, imidazo-4-yl, morpholin-3-yl, oxazolyl, isoxazolyl, thiazolyl, tetrazolyl, which can be unsubstituted or substituted with $C_{1-4}$alkyl, or $R^{14}$, $R^{15}$, and the intervening nitrogen atom together can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

A is N or CH;

X and Y are either N or C, provided that X and Y cannot be the same;

and the dashed bonds denote a single or double bond.

2. The compound of claim 1 wherein the compound is selected from the group consisting of: (S)-2-(8,9-dihydro-9-methyl-7H-[1,4]oxazino[2,3-g]indazol-1-yl)-1-methyl-ethylamine fumarate; 1-((S)-2-Aminopropyl)-1,9-dihydro-7H-[1,4]oxazino[2,3-g]indazol-8-one hydrochloride; 1-((S)-2-Aminopropyl)-1,9-dihydro-9-methyl-7H-[1,4]oxazino[2,3-g]indazol-8-one hydrochloride; and [1-[(2S)-2-aminopropyl]-9-methyl-1,7,8,9-tetrahydro[1,4]oxazino[2,3-g]indazol-8-yl]methanol.

* * * * *